United States Patent [19]
Dandge et al.

[11] Patent Number: 5,457,056
[45] Date of Patent: * Oct. 10, 1995

[54] HALOHYDROCARBON SENSING CHEMISTRY WITH BASE MODIFIER

[75] Inventors: Dileep K. Dandge; Kishology Goswami; Stanley M. Klainer, all of Henderson; Chuka H. Ejiofor, Las Vegas, all of Nev.

[73] Assignee: FiberChem, Inc., Las Vegas, Nev.

[*] Notice: The portion of the term of this patent subsequent to Oct. 25, 2011 has been disclaimed.

[21] Appl. No.: 88,193

[22] Filed: Jul. 6, 1993

[51] Int. Cl.⁶ .......................... G01N 21/78; G01N 21/64
[52] U.S. Cl. .................... 436/166; 436/106; 436/111; 436/126; 436/172
[58] Field of Search .................................. 436/106, 111, 436/126, 166, 172

[56] References Cited

U.S. PATENT DOCUMENTS

| | | |
|---|---|---|
| 4,666,672 | 5/1987 | Miller et al. ............................. 422/68 |
| 4,771,006 | 9/1988 | Miller et al. ............................ 436/126 |
| 4,916,237 | 4/1990 | Lee et al. ................................. 549/76 |
| 4,929,562 | 5/1990 | Anderson ............................... 436/126 |
| 4,960,711 | 10/1990 | Aoki et al. ............................. 436/124 |
| 5,094,817 | 3/1992 | Aoki et al. ............................. 422/68.1 |
| 5,196,424 | 3/1993 | Gossett et al. ......................... 514/258 |

*Primary Examiner*—Robert J. Warden
*Assistant Examiner*—N. Bhat
*Attorney, Agent, or Firm*—Henry P. Sartorio

[57] ABSTRACT

A base modifier is added to a pyridine/base reagent composition to improve the ability to detect halogenated hydrocarbons like TCE and chloroform. The base modifier is an organic base which facilitates formation of a stable final reaction product. New bases are also combined with pyridine.

15 Claims, 9 Drawing Sheets

HALOHYDROCARBON SENSING CHEMISTRY WITH BASE MODIFIER

BACKGROUND OF THE INVENTION

The invention relates generally to the chemical detection of halogenated hydrocarbons (halohydrocarbons) and more particularly to the detection of halohydrocarbons, including certain organic chlorides, using a Fujiwara-like reaction.

Trichloroethylene (TCE) heads the U.S. Environmental Protection Agency's (EPA) list of hazardous (toxic, carcinogenic, etc.) compounds and the organic chlorides, as a group, dominate the ten (10) most frequently found dangerous compounds. The other organic chlorides include 1,1,1-trichloroethane (TCA), 1,1,2,2-tetrachloroethane, chloroform ($CHCl_3$), carbon tetrachloride ($CCl_4$) and 1,2-dichloroethylene (DCE). Thus, the detection of these compounds is extremely important.

The Fujiwara reaction is a known methodology widely used for the fluorometric and colorimetric analysis of gem-polyhalogen compounds. In the presence of a strong alkali ($OH^-$), such as sodium or potassium hydroxide, pyridine or a derivative thereof reacts with a halogenated hydrocarbon to produce a red colored fluorescent product. The traditional chemistry (pyridine/alkali metal base) is a two-phase system, since the commonly used aqueous alkalis (NaOH or KOH) are not miscible with pyridine. Therefore, the reaction product is formed only at the interface. The Fujiwara chemistry has been modified to overcome the limitations of the two-phase system. U.S. Pat. No. 4,929,562 to Anderson (deceased) et al. shows a single-phase system which utilizes pyridine or a derivative thereof with a hindered nitrogen base (phase transfer catalyst), particularly a tetra alkyl ammonium hydroxide (quaternary ammonium base). The organic bases (with bulkier counterions) have increased solubility in pyridine so that a single phase is achieved. However, in both cases above, the hydroxide ion serves as the base. The chemistry is usually species specific but not compound specific.

The detectable red reaction product using either the original Fujiwara chemistry or the chemistry as modified by Anderson is short lived and quickly converts to a light yellow final product which is difficult to detect. It is desirable to modify the sensing chemistry of Fujiwara or Anderson to overcome the deficiencies of the prior art and to produce a stable reaction product which is easy to detect.

SUMMARY OF THE INVENTION

The invention is a pyridine/base reagent composition or sensing chemistry which includes an organic base modifier. The base modifier is added to the combination of pyridine or pyridine derivatives and alkali metal hydroxides or quaternary ammonium hydroxides. The base modifier is preferably a pyrimidine or other nitrogen heterocyclic compound. The invention also includes the substitution of other bases for the conventional base, and further includes a base modifier with the new bases.

DETAILED DESCRIPTION OF THE PREFERRED EMBODIMENTS

The sensing chemistry according to the invention is the combination of (1) an indicator or color forming reactant selected from pyridine and derivatives thereof (substituted pyridines) (2) a base selected from an alkali metal hydroxide, a quaternary ammonium hydroxide or another base, and (3) an organic base modifier selected from a pyrimidine or other nitrogen heterocyclic compound. The base is MOH where M=alkali metal as in the traditional Fujiwara chemistry, or QAOH where QA=quaternary ammonium cation, particularly tetraalkyl ammonium hydroxides. The base may also be sodium thiophenoxide or other phenoxides and thiocresolates with or without the organic base modifier. The organic base modifier is a pyrimidine or derivative thereof, including hexahydro pyrimido pyrimidine (HPP) and hexahydro methyl pyrimido pyrimidine (HMPP), or another nitrogen heterocyclic compound, including acetaldehyde ammonia trimer, 1,5-diazabicyclo[4.3.0]non-5-ene, 1,4-diazabicyclo [2.2.2]octane, 1,8-diazabicyclo[5.4.0]undec-7-ene.

The modifier is also a strong organic base. The combination of the modifier with the Fujiwara/Anderson bases overcomes the problem of the prior art that the detection product formed is an intermediate product that quickly converts to a final product which is difficult to detect. The prior art chemistry produces the following products:

The red intermediate product which absorbs at 550 nm is relatively easy to detect because inexpensive sources and detectors are available at this wavelength. However, the final product which absorbs at 360–370 nm is difficult to detect because of the requirement of near UV sources/detectors. Thus, the unstable intermediate product must be detected rather than the stable final product. With the chemistries according to the invention, the following illustrative product is obtained:

The final product absorbs at 410–440 nm, which is easy to detect using blue source/detector. The modifier in combination with the other base functions to affect the reaction to open the pyridine ring which leads to formation of the final product.

The addition of the modifier also provides greater selectivity to particular halohydrocarbon species. The final product can differ in color depending on the halohydrocarbon. For example, the final product could absorb at another wavelength, e.g., 500–550 nm. For example, without the modifier, both $CHCl_3$ and TCE produce a pink detection product so they cannot be distinguished. However, with particular chemistries with a modifier, the product for $CHCl_3$ is pink while the TCE product is yellow, so the species can be easily distinguished.

In solution, the pyridine or pyridine derivative is typically in the range of about 60–90% (v/v), with the remaining volume being the other components. The following are examples of specific compositions:

EXAMPLE 1

| | |
|---|---|
| Indicator: | Pyridine |
| Base: | tetrabutylammonium hydroxide (1 drop) |
| Modifier: | HPP (0.01 to 1 M and preferably 0.1 M molar) in pyridine |

Figure 1:
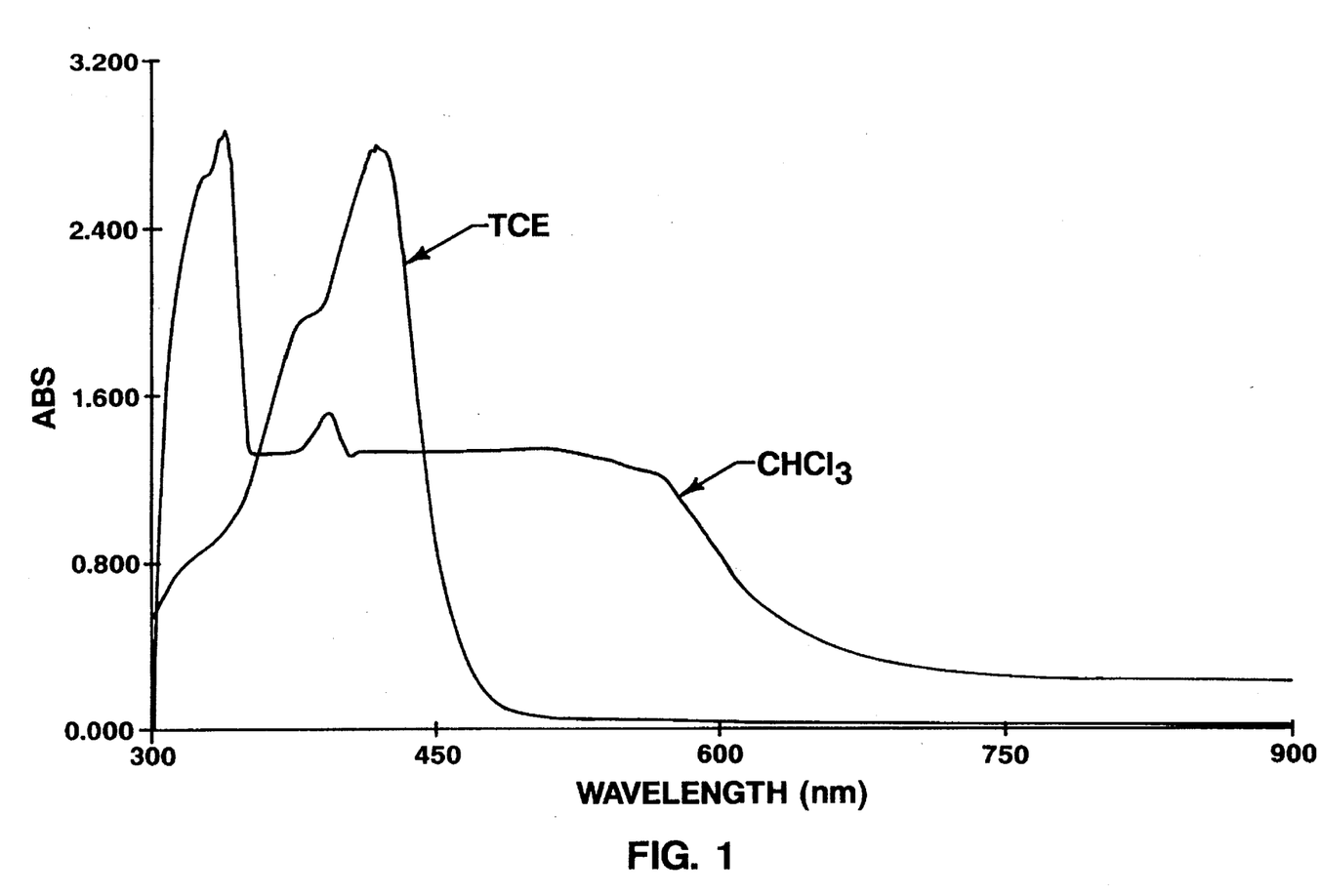
FIGS. 1–7 are absorption spectra for TCE and $CHCl_3$ with various chemistries.

The absorption spectrum for TCE and $CHCl_3$ is shown in FIG. 1.

EXAMPLE 2

| | |
|---|---|
| Indicator: | Pyridine |
| Base: | NaOH, 0.1 M (1 drop) |
| Modifier: | HPP (0.1 M) in pyridine |

Figure 2:
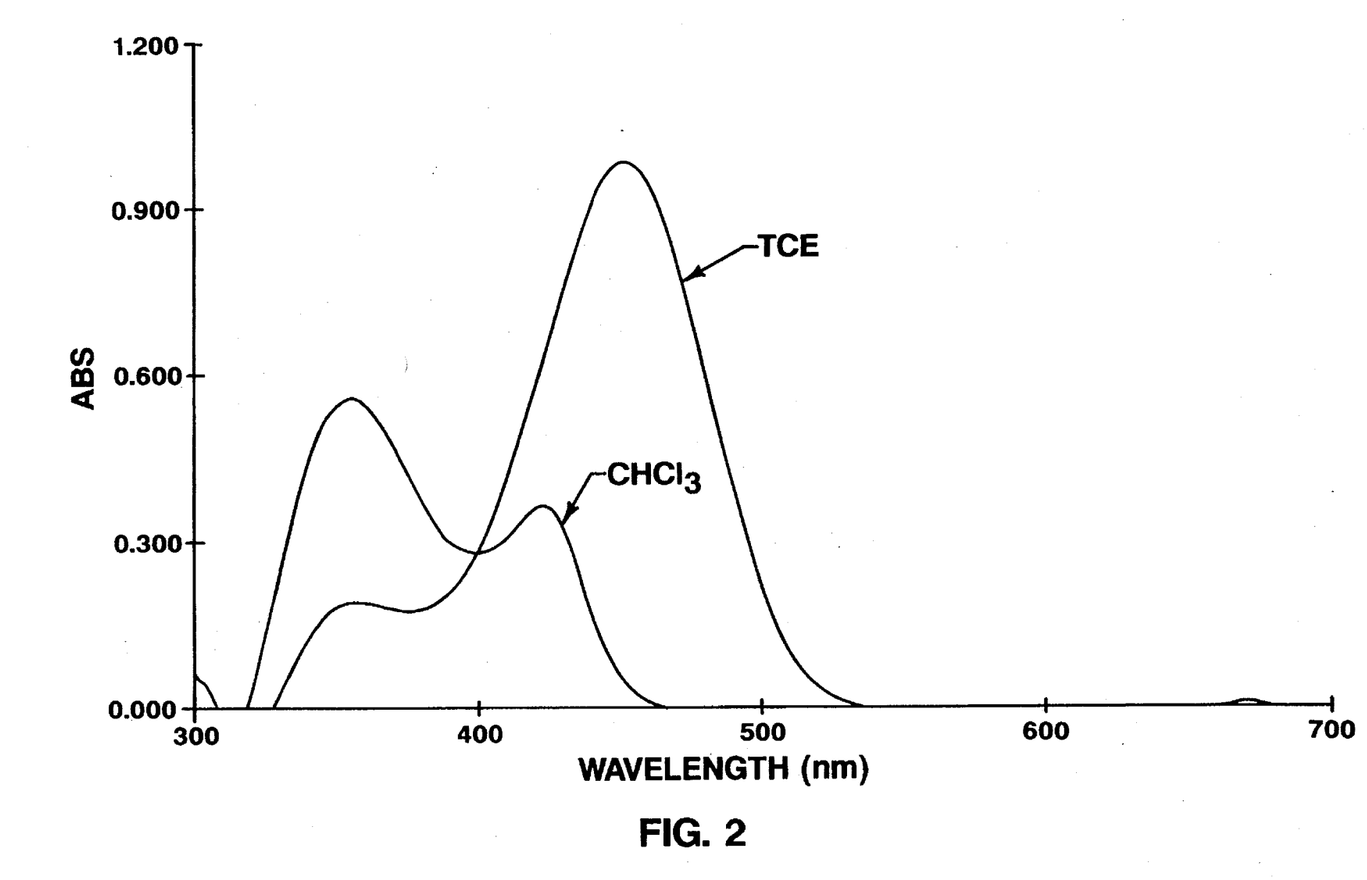

The absorption spectrum for TCE and $CHCl_3$ is shown in FIG. 2.

EXAMPLE 3

| | |
|---|---|
| Indicator: | Pyridine |
| Base: | NaOH 0.1 M (1 drop) |
| Modifier: | HMPP (0.1 M) in pyridine |

Figure 3:
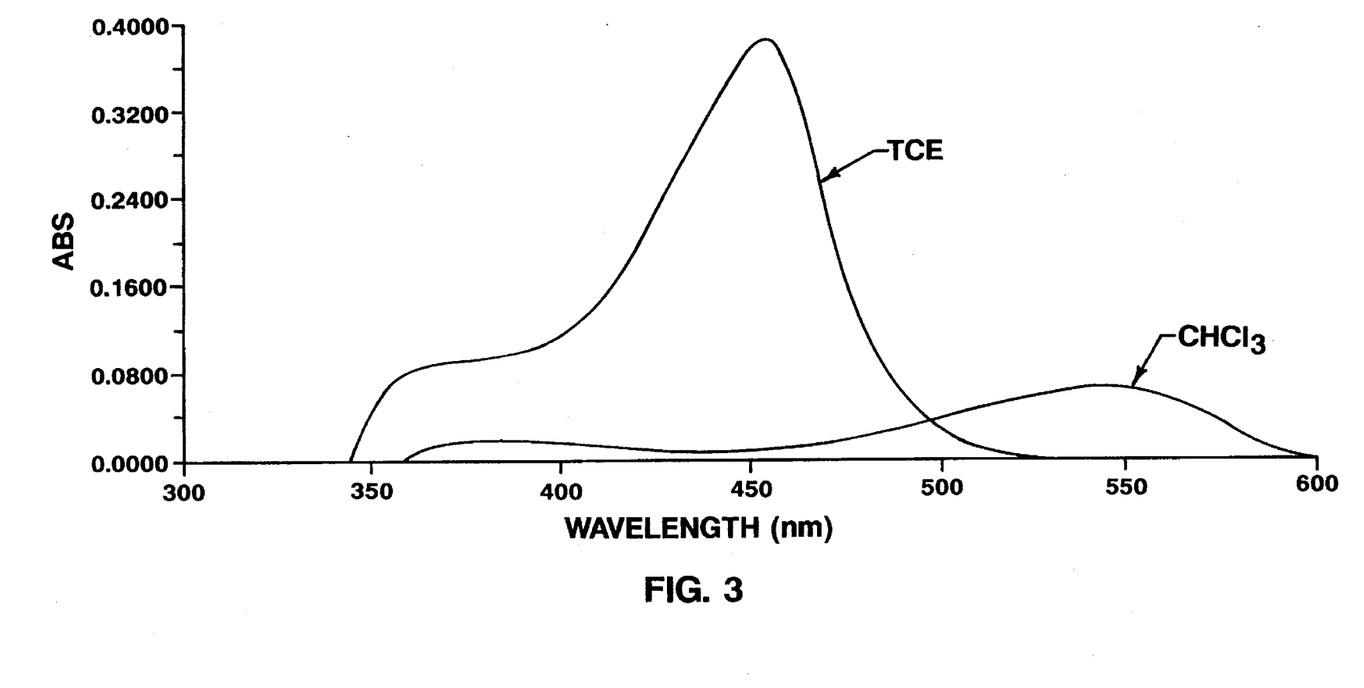

The absorption spectrum for TCE and $CHCl_3$ is shown in FIG. 3.

EXAMPLE 4

| | |
|---|---|
| Indicator: | 4,4-Trimethylene dipyridine (20 wt. %) |
| Base: | tetrabutylammonium hydroxide |
| Modifier: | (A) None, (B) HPP 0.1 M, (C) HMPP 0.1 M |

Figure 4A:
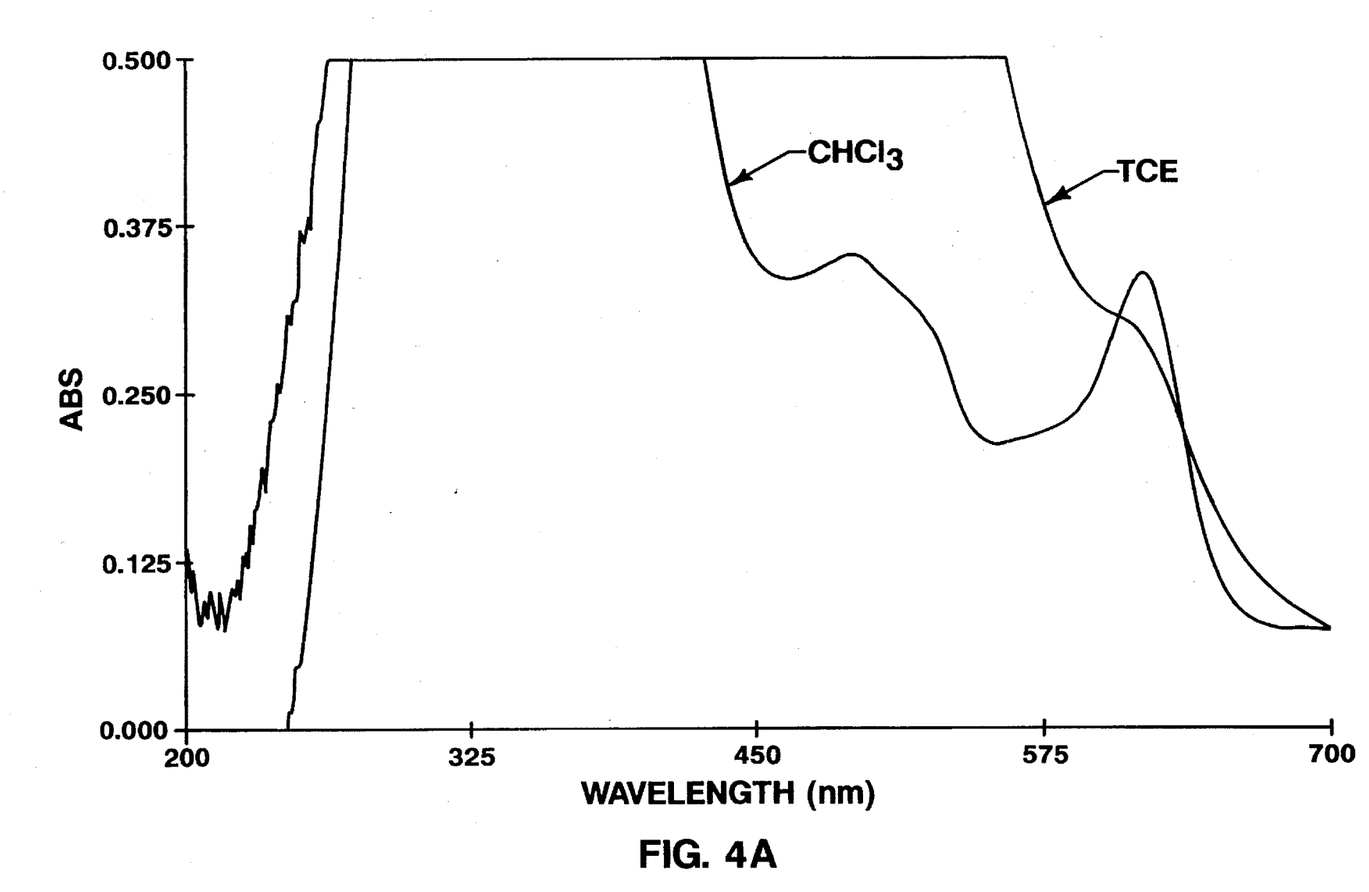
Figure 4B:
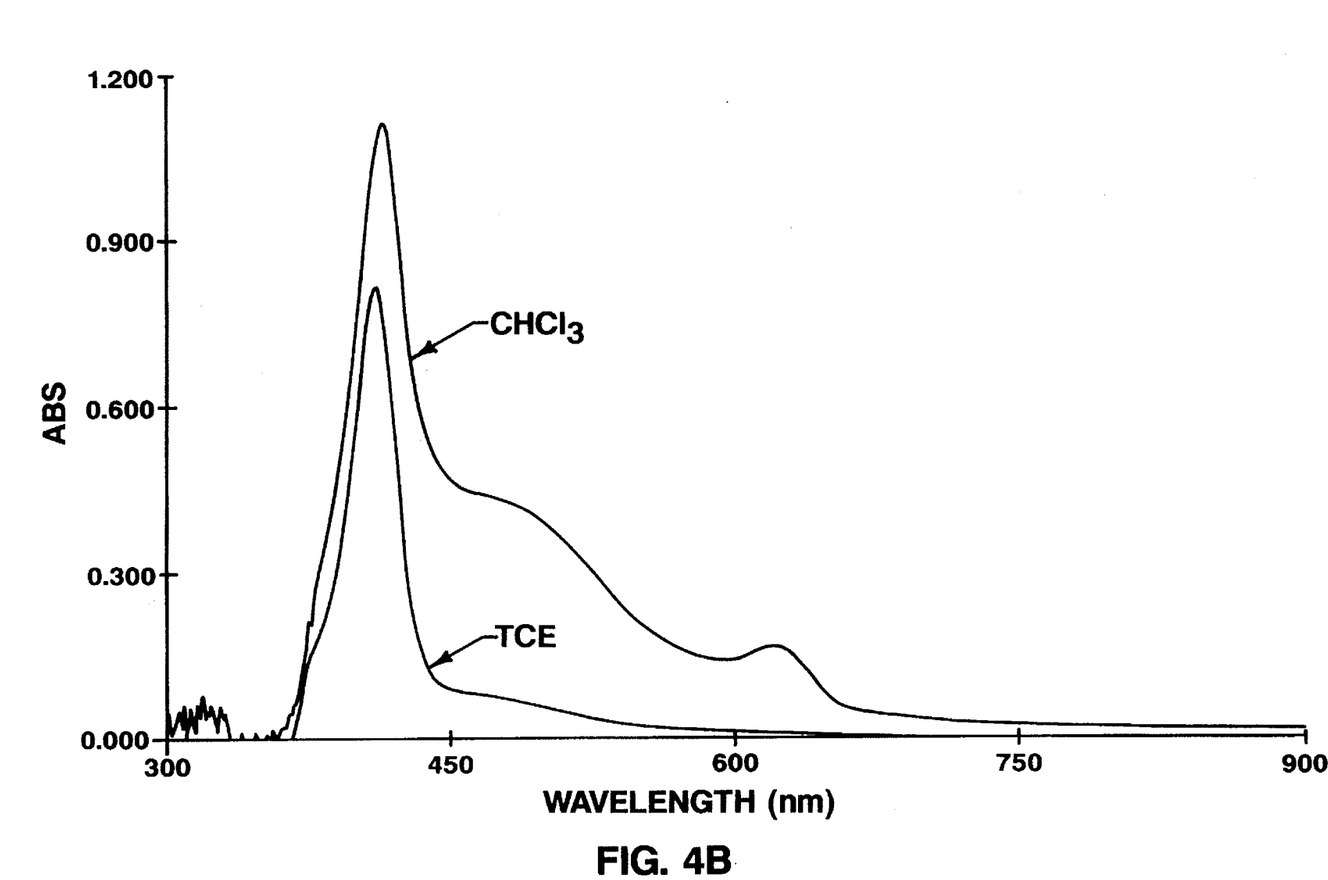
Figure 4C:
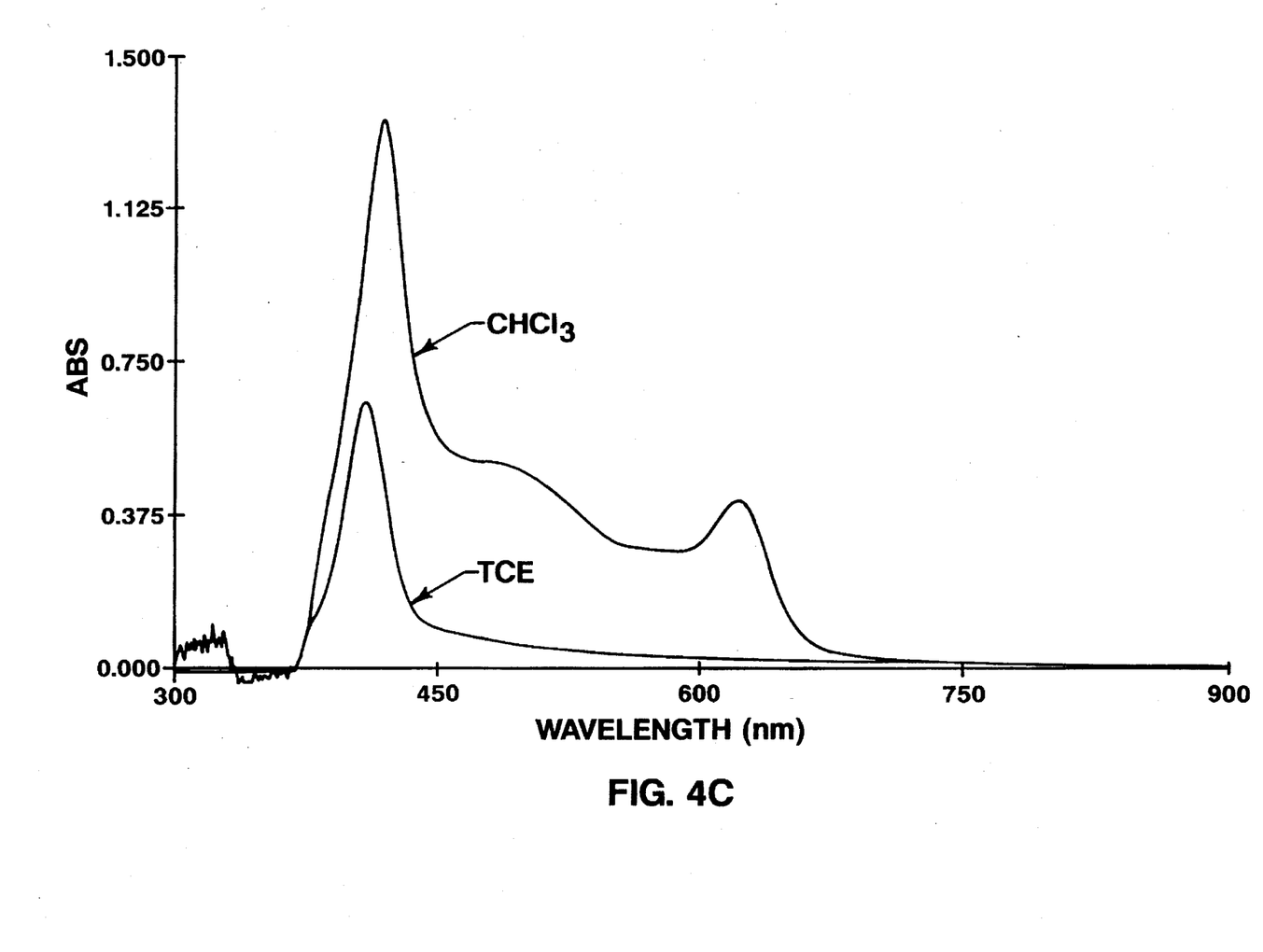

The absorption spectra for TCE and $CHCl_3$ with modifiers (A), (B) and (C) are shown in FIGS. 4A–C, respectively.

EXAMPLE 5

| | |
|---|---|
| Indicator: | Pyridine |
| Base: | tetrabutylammonium hydroxide (1 drop) |
| Modifier: | Acetaldehyde ammonia trimer (5 wt. %) |

Figure 5:
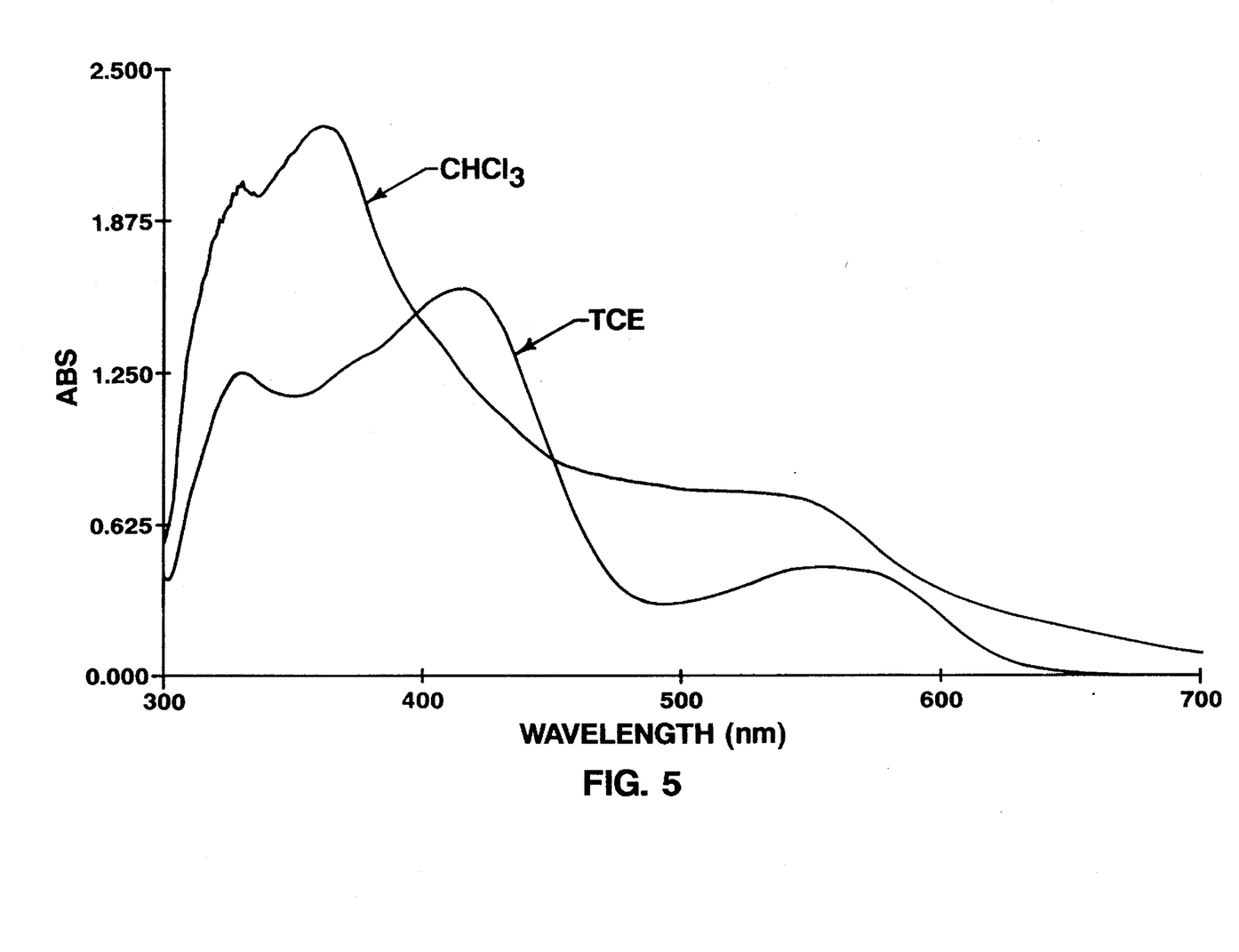

The absorption spectrum for TCE and $CHCl_3$ is shown in FIG. 5.

EXAMPLE 6

| | |
|---|---|
| Indicator: | Pyridine |
| Base: | tetrabutylammonium hydroxide (1 drop) |
| Modifier: | 1,8-Diazabicyclo[4.3.0]undec-7-ene or 1,5-diazabicyclo[4.3.0]non-5-ene |

Figure 6:
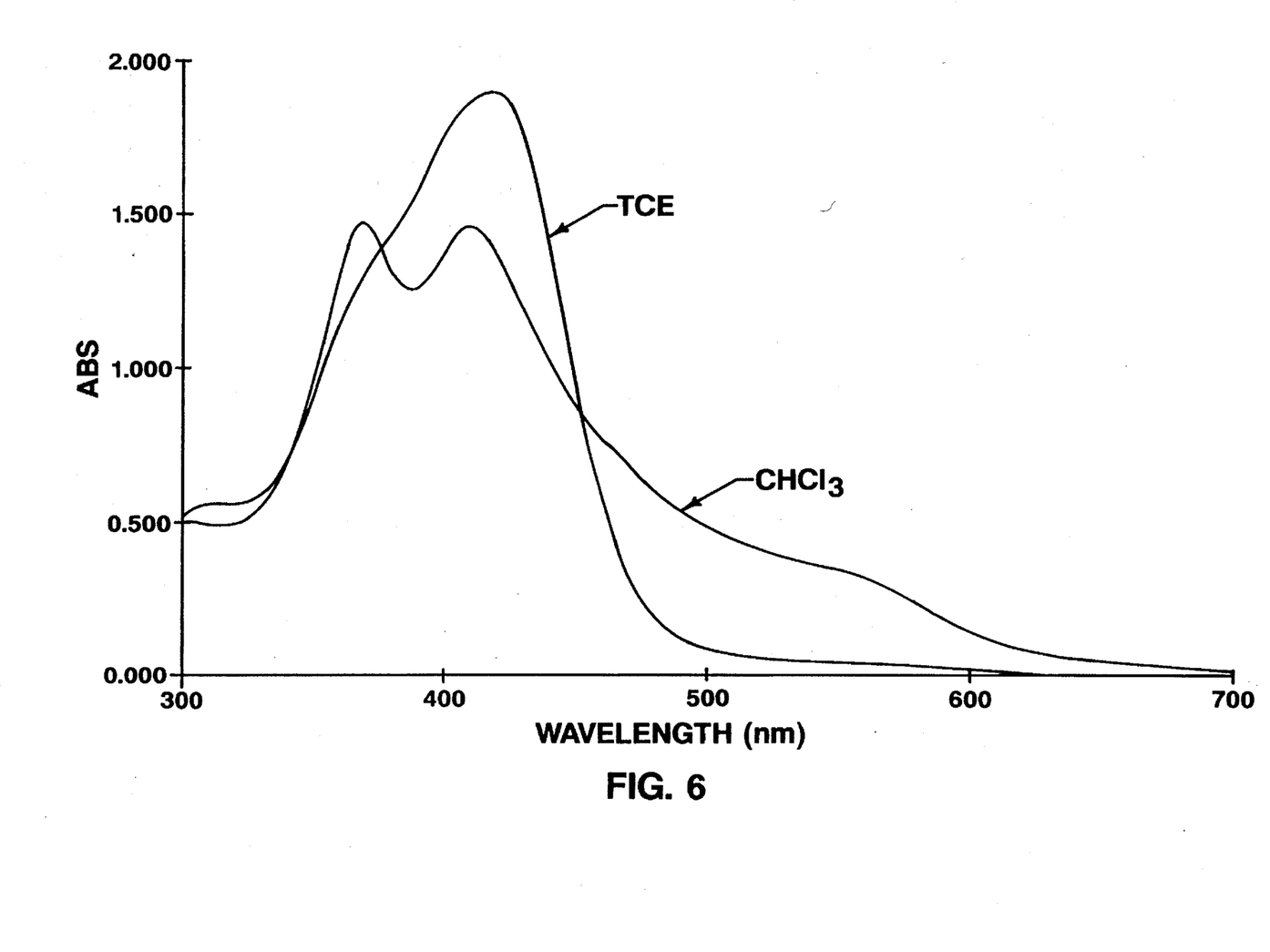

The absorption spectrum for TCE and $CHCl_3$ is shown in FIG. 6.

EXAMPLE 7

| | |
|---|---|
| Indicator: | Pyridine |
| Base: | tetrapropylammonium hydroxide (1 drop) |
| Modifier: | 1,8-Diazabicyclo[4.3.0]undec-7-ene or 1,5-diazabicyclo[4.3.0]non-5-ene |

Figure 7:
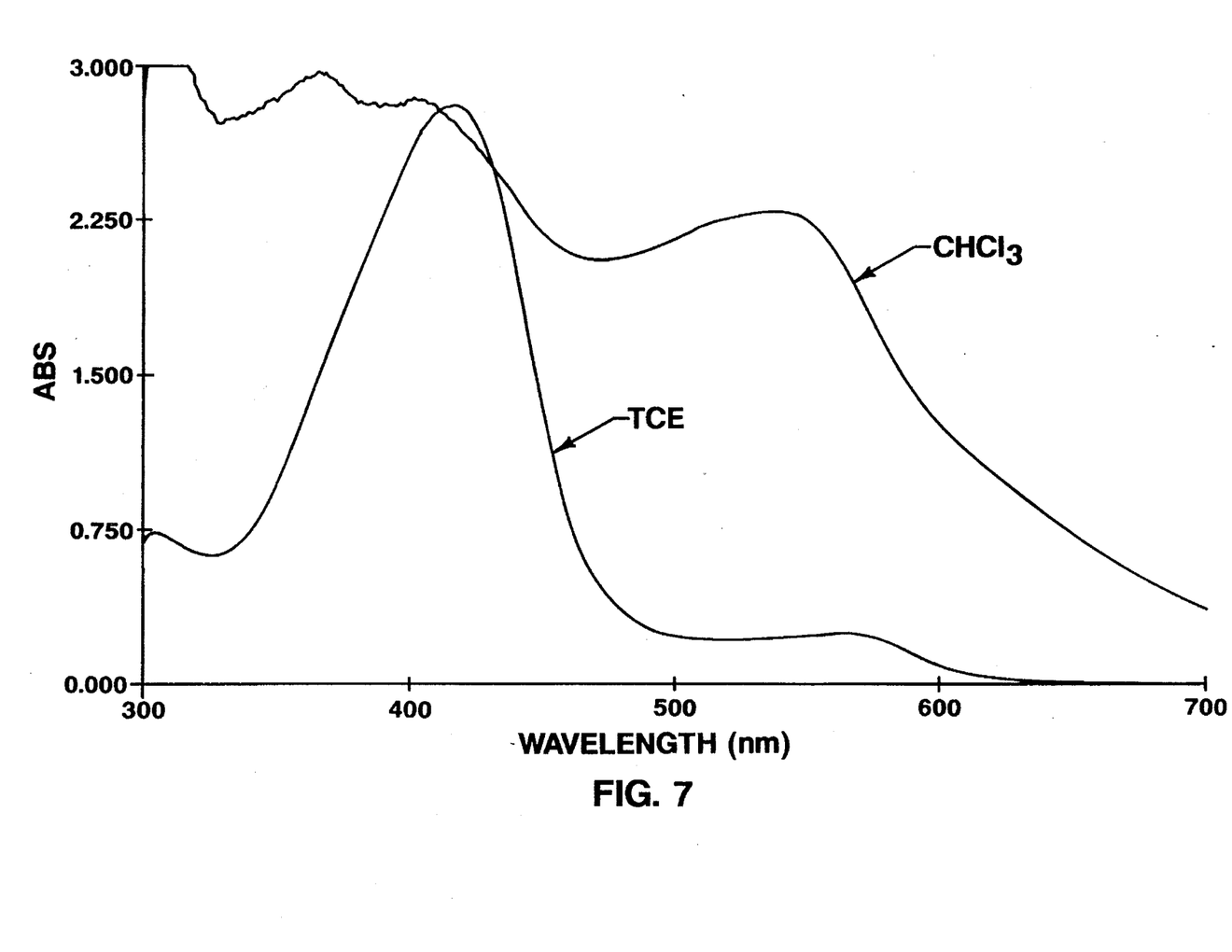

The absorption spectrum for TCE and $CHCl_3$ is shown in FIG. 7.

Changes and modifications in the specifically described embodiments can be carried out without departing from the scope of the invention which is intended to be limited only by the scope of the appended claims.

We claim:

1. A method for detecting halogenated hydrocarbon comprising:

providing a sensing chemistry comprising a pyridine or a substituted pyridine, a base selected from the group consisting of phenoxide, and a base modifier selected from the group consisting of pyrimidines, acetaldehyde ammonia trimer, 1,8-diazabicyclo[ 4.3.0]undec-7-ene, and 1,5-diazabicyclo[4.3.0]non-5-ene;

contacting the sensing chemistry with a halogenated hydrocarbon;

detecting the presence of a reaction product of the halogenated hydrocarbon and pyridine or substituted pyridine.

2. The method of claim 1 further comprising detecting the reaction product colorimetrically.

3. The method of claim 2 further comprising detecting the reaction product by measuring absorption at about at least one of 410–440 nm and 510–550 nm.

4. A sensing chemistry for detecting halogenated hydrocarbons, comprising:

a pyridine or substituted pyridine;

a first base selected from the group consisting of alkali metal hydroxides, quaternary ammonium hydroxides and phenoxides;

a second base selected from the group consisting of pyrimidines, acetaldehyde ammonia trimer, 1,8-diazabicyclo[4.3.0]undec-7-ene, and 1,5-diazabicyloc[4.3.0]non-5-ene.

5. The sensing chemistry of claim 4 wherein the first base is selected from the group consisting of alkali metal hydroxides and tetra alkyl ammonium hydroxides.

6. The sensing chemistry of claim 4 wherein the first base is selected from the group consisting of phenoxides.

7. The sensing chemistry of claim 6 wherein the phenoxide is sodium thiophenoxide.

8. The sensing chemistry of claim 4 wherein the second base is a pyrimidine.

9. The sensing chemistry of claim 8 wherein the second base is hexahydro pyrimido pyrimidine or hexahydro methyl pyrimido pyrimidine.

10. The sensing chemistry of claim 4 wherein the second base is acetaldehyde ammonia trimer or 1,8-diazabicyclo[4.3.0]undec-7-ene or 1,5-diazabicyclo[4.3.0]non-5-ene.

11. A sensing chemistry for detecting halogenated hydrocarbons, comprising:

pyridine or a substituted pyridine;

a base selected from the group consisting of phenoxides.

12. The sensing chemistry of claim 11 wherein the phenoxide is sodium thiophenoxide.

13. The sensing chemistry of claim 11 wherein the sensing chemistry further comprises a nitrogen heterocyclic compound selected from the group consisting of acetaldehyde ammonia trimer, 1,8,-diazabicyclo[4.3.0]undec-7-ene, and 1,5-diazabicyclo[4.3.0]non-5-ene.

14. The sensing chemistry of claim 11 wherein the sensing chemistry further comprises a pyrimidine.

15. The sensing chemistry of claim 14 wherein the pyrimidine is hexahydro pyrimido pyrimidine or hexahydro methyl pyrimido pyrimidine.

* * * * *